United States Patent [19]

Maruta et al.

[11] Patent Number: 4,987,259

[45] Date of Patent: Jan. 22, 1991

[54] PROCESS OF PREPARING 2,2-BIS(4-AMINOPHENYL)-HEXAFLUOROPROPANE

[75] Inventors: Masamichi Maruta; Showzou Kaneda; Mineo Watanabe; Etsuko Katoh, all of Kawagoe, Japan

[73] Assignee: Central Glass Company, Limited, Ube, Japan

[21] Appl. No.: 360,981

[22] Filed: Jun. 2, 1989

[30] Foreign Application Priority Data

Jun. 10, 1988 [JP] Japan .................. 63-141822

[51] Int. Cl.$^5$ ........................................ C07C 321/00
[52] U.S. Cl. ............................................ 564/335
[58] Field of Search ................................ 564/338

[56] References Cited

U.S. PATENT DOCUMENTS 3,310,573  3/1967  Coe .
4,370,501  1/1983  Lau .

OTHER PUBLICATIONS

"Synthesis of Fluorinated Bifunctional Monomers", by D. I. Mendeleeva, Chem. Abstracts, vol. 65, #18523a.
Adams et al., "Organic Reactions", vol. 3, pp. 373, 375-380 and 388 (1956).
Starks et al., "Phase Transfer Catalysis", pp. 155-157 (1978).

*Primary Examiner*—Robert V. Hines
*Attorney, Agent, or Firm*—Fleit, Jacobson, Cohn, Price, Holman & Stern

[57] ABSTRACT

2,2-Bis(4-aminophenyl)hexafluoropropane is prepared by the steps of (a) reacting 2,2-bis(4-carboxyphenyl)-hexafluoropropane with thionyl chloride at 80°–150° C. in a water insoluble organic liquid in the presence of a catalyst such as dimethylformamide to obtain a solution of 2,2-bis(4-chloroformylphenyl)hexafluoropropane, (b) mixing the obtained solution with an aqueous solution of sodium azide to obtain an acid azide solution, (c) heating the organic phase of the acid azide solution to 80° C. or above to cause rearrangement of the acid azide into an isocyanate, (d) hydrolyzing the isocyanate by mixing the isocyanate solution with an acid such as 40–80% sulfuric acid to form a salt of the aimed diamine as an aqueous solution mixed with an organic phase, and (e) neutralizing the aqueous solution separated from the liquid mixture obtained at step (d) to precipitate the aimed diamine. This process is favorable for industrial practice because the main steps (a) to (d) are all reactions in organic liquids without precipitating solid intermediates.

7 Claims, No Drawings

PROCESS OF PREPARING 2,2-BIS(4-AMINOPHENYL)-HEXAFLUOROPROPANE

BACKGROUND OF THE INVENTION

This invention relates to a process of preparing 2,2-bis(4-aminophenyl)hexafluoropropane which is a compound useful as the material of some fluororesins such as fluorine-containing polyimides.

U.S. Pat. No. 4,370,501 shows preparing 2,2-bis(4-aminophenyl)hexafluoropropane by the steps of converting potassium salt of 2,2-bis(4-hydroxyphenyl)hexafluoropropane into a 4-chloro-2-phenylquinazoline in dimethylsufoxide and isolateing the quinazoline, converting the quinazoline into a bisquinazolinone by heating at about 320° C. and hydrolyzing the quinazolinone to thereby obtain the aimed compound. However, this process is not suitable for industrial practice because of using expensive reagents and including reactions which must be carried out under severe conditions.

Zh. Vses. Khin. Obshchestva im. D. I. Mendeleeva, 11(4), 469(1966) shows that 2,2-bis(4-aminophenyl)hexafluoropropane is obtained from 2,2-bis(4-methylphenyl)hexafluoropropane, which can be prepared relatively easily, by the steps of oxidizing the starting compound by dilute nitric acid to obtain a corresponding carboxylic acid, converting the obtained acid into an acid chloride by reaction with thionyl chloride, mixing an acetone solution of the acid chloride with an aqueous solution of sodium azide to precipitate an acid azide and recovering it by filtration, heating the acid azide in xylene to cause rearrangement into an isocyanate and distilling the reaction liquid to isolate the isocyanate and hydrolyzing the isocyanate by hydrochloric acid to thereby obtain the aimed diamine. However, this process is unfavorable for industrial practice because of having many steps, including troublesome operations for separating solid intermediates and needing isolation of the intermediately formed isocyanate, which has a high boiling point, by distiallation.

U.S. Pat. No. 3,310,573 shows preparing 2,2-bis(4-aminophenyl)hexafluoropropane by the steps of oxidizing 2,2-bis(4-methylphenyl)hexafluoropropane in acetic acid by chromium trioxide to obtain a corresponding carboxylic acid, suspending the carboxylic acid in a mixture of sulfuric acid and chloroform and adding hydrogen azide to the suspension to thereby convert the carboxylic acid into an acid azide, heating the acid azide to form an isocyanate as an intermediate and then obtain sulfate of the aimed diamine. This process consists of a relatively small number of steps, but it is a disadvantage to use a large amount of hydrogen azide which is instable and highly toxic.

SUMMARY OF THE INVENTION

It is an object of the present invention to provide an industrially favorable process for preparing 2,2-bis(4-aminophenyl)hexafluoropropane.

The present invention provides a process of preparing 2,2-bis(4-aminophenyl)hexafluoropropane from 2,2-bis(4-carboxyphenyl)hexafluoropropane, which is relatively easy to prepare, by several reactions all of which can be carried out in liquid media without need of isolating solid intermediates and without using a very toxic reagent such as hydrogen azide.

More definitely, the present invention is a process of preparing 2,2-bis(4-aminophenyl)hexafluoropropane by the steps of (a) reacting 2,2-bis(4-carboxyphenyl)hexafluoropropane with thionyl chloride at a temperature in the range from 80° to 150° C. in an organic liquid, which is insoluble in water and has a boiling point higher than the aforementioned temperature, in the presence of a catalyst selected from amines and amides to thereby obtain a solution of 2,2-bis(4-chloroformylphenyl)hexafluoropropane, (b) mixing the solution obtained at step (a) with an aqueous solution of sodium azide to thereby obtain an acid azide solution, (c) separating an aqueous phase from the acid azide solution to leave an organic phase and heating the organic phase to a temperature not lower than 80° C. to cause rearrangement of the acid azide to thereby obtain an isocyanate solution, (d) hydrolyzing the isocyanate solution under an acidic condition to thereby form a salt of 2,2-bis(4-aminophenyl)hexafluoropropane as an aqueous solution mixed with an organic phase, and (e) separating the aqueous solution formed at step (d) from the organic phase and neutralyzing the separated aqueous solution to thereby precipitate 2,2-bis(4-aminophenyl)hexafluoropropane.

In the process according to the invention the main steps (a) to (d) are all reactions in organic liquids without precipitating solid products. There is no need for a troublesome operation for separation of a solid from a reaction liquid except the filtration operation at step (e) for recoverying the aimed product, and the process includes no distillation operation for isolating an intermediate. Although this process has a relatively large number of steps, as a whole the process is easy to perform and high in efficiency or productivity since all the reactions can be carried out consecutively by merely performing separation of an aqueous phase from an organic phase after step (b) and after step (d). During the consecutive reactions loss of the intermediates is very small, and consequently the aimed diamine can be obtained at very good yield.

DESCRIPTION OF THE PREFERRED EMBODIMENTS

At the first step of the process according to the invention the reaction between 2,2-bis(4-carboxyphenyl)hexafluoropropane and thionyl chloride in a water insoluble organic liquid medium proceeds readily and completely when the reaction system is kept heated at a temperature not lower than 80° C., and preferably not lower than 90° C. However, it is undesirable that the reaction temperature exceeds 150° C. because of a considerable increase in the loss of thionyl chloride. The orgainc liquid medium must have a boiling point higher than the employed reaction temperature. Good examples of organic solvents useful for this reaction are toluene, xylene and chlorobenzene. As to the proportions of the reactants, it suffices to use 2 to 2.3 mols of thionyl chloride per mol of 2,2-bis(4-carboxyphenyl)hexafluoropropane. As a catalyst for this reaction an amine or an amide is used. It is preferred to use dimethylformamide or dimethylacetamide as the catalyst. It suffices that the catalyst amounts to 0.01–1 wt % of 2,2-bis(4-carboxyphenyl)hexafluoropropane.

At the second step of the process it is suitable to carry out the reaction at a temperature in the range from 0° to 40° C. using sodium azide in a quantity approximately equivalent to thionyl chloride used at the first step. For raising the rate of the reaction it is preferable to use an ammonium salt or a phosphonium salt which acts as a phase-transfer catalyst. It suffices that the catalyst amounts to about 1 wt % of sodium azide.

At the start of the third step, the acid azide solution obtained at the second step is separated into an aqueous phase and an organic phase. The aqueous phase is discarded, and the organic phase is thoroughly dried by using a suitable dessicant such as anhydrous magnesium sulfate, anhydrous sodium sulfate or anhydrous calcium chloride. After that the organic phase is heated to 80° C. or above for accomplishment of a rearrangement reaction to form an isocyanate. Since this rearrangement reaction is an exothermic reaction, care should be taken to dissipate heat generated by the reaction to thereby prevent a rapid rise in temperature. In this regard it is desirable to carry out the reaction by gradually introducing the acid azide solution into a reactor in which heating is effected.

At the fourth step an acid is used for the hydrolysis of the isocyanate. As the acid it is preferred to use sulfuric acid 40–80% in concentration. It is suitable to use 5–25 mols of sulfuric acid (as $H_2SO_4$) per mol of 2,2-bis(4-carboxyphenyl)hexafluoropropane subjected reaction at the first step. It is suitable to carry out the hydrolyzing reaction at a temperature not lower than 80° C., and preferably not lower than 100° C. This reaction is an exothermic reaction. It is desirable to carry out the reaction by gradually introducing the isocyanate solution heated to a suitable temperature into sulfuric acid, and also it is desirable to prevent carbon dioxide gas formed by the reaction from accumulating in the reactor.

At the fifth (last) step, the diamine salt solution obtained at the fourth step is separated into an organic phase and an aqueous phase containing sulfuric acid and sulphate of the aimed diamine. The aqueous phase is neutralized by the addition of a suitable alkali to thereby precipitate the aimed diamine, 2,2-bis(4-aminophenyl)-hexafluoropropane, and the precipitated product is recovered by filtration.

The invention is further illustrated by the following nonlimitative example.

EXAMPLE

A 3-liter three-necked flask, which was provided with a mechanical stirrer, condenser, liquid dropping nozzle and thermometer, was charged with 1 liter of toluene, 500 g of 2,2-bis(4-carboxyphenyl)hexafluoropropane and 1 ml of dimethylformamide, and the mixture was heated up to 60° C. Then 370 g of thionyl chloride was slowly dropped into the flask in 2 hr while stirring was made. After that the temperature of the liquid in the flask was raised to 100° C., and at this temperature stirring was continued for 1.5 hr to thereby complete the reaction of the starting compound with thionyl chloride. After cooling the reaction liquid was subjected to HPLC analysis to find that the conversion of the starting compound into 2,2-bis(4-chloroformyl-phenyl)hexafluoropropane was more than 98%.

In another 3-liter three-necked flask 250 g of sodium azide was dissolved in 500 ml of water, and 5 g of benzyltriethylammonium chloride was added as a phase-transfer catalyst. The flask containing the sodium azide solution was kept cooled with ice, and the reaction liquid containing the product of the initial reaction was slowly dropped into the sodium azide solution in 2 hr while stirring was made. After that the mixed liquid was stirred for 1 hr. By HPLC analysis the conversion of the carboxylic acid chloride into acid azide was found to be more than 98%.

The reaction liquid containing the acid azide was separated into an aqueous phase and an organic phase, and the organic phase was separated from the aqueous phase and dried by anhydrous magnesium sulfate. A portion (150 ml) of the dried orgainc liquid was charged into a 3-liter three-necked flask and heated up to 90° C. to cause rearrangement of the acid azide into an isocyanate. Continuing stirring of the heated liquid, the remaining portion of the dried organic liquid was slowly dropped into the heated liquid in 3 hr. After that the whole liquid was stirred at 100° C. for 1 hr to thereby complete the rearrangement reaction. By HPLC analysis the rearrangement of the acid azide into isocyanate was found to be more than 98%.

After the above rearrangement reaction the reaction liquid was slowly dropped into 750 ml of 67% sulfuric acid, which was kept heated at 100° C., in 2.5 hr while stirring was made. After that stirring of the mixed liquid was continued for 1 hr to thereby complete the hydrolyzing reaction. By HPLC analysis the conversion of the isocyanate into sulfate of 2,2-bis(4-aminophenyl)-hexafluoropropane was found to be more than 98%. The reaction liquid was separated into an organic phase and an acidic aqueous phase. The acidic aqueous phase was neutralized by slowly dropping it into 4 kg of 20% aqueous solution of NaOH in 4.5 hr. This treatment caused precipitation of a white powder. The precipitate was separated from the mother liquor by filtration and dried to obtain 410 g of 2,2-bis(4-aminophenyl)hexafluoropropane of 98.4% purity. The yield of the product amounted to 95.3%.

What is claimed is:

1. A process of preparing 2,2-bis(4-aminophenyl)hexafluoropropane, comprising the steps of:
   (a) reacting 2,2-bis(4-carboxyphenyl)hexafluoropropane with thionyl chloride at a temperature in the range from 80° to 150° C. in an organic liquid, which is insoluble in water and has a boiling point higher than said temperature, in the presence of a catalyst selected from amines and amides to thereby obtain a solution of 2,2-bis(4-chloroformyl-phenyl)hexafluoropropane;
   (b) mixing the solution obtained at step (a) with an aqueous solution of sodium azide to thereby obtain an acid azide solution;
   (c) separating an aqueous phase from said acid azide solution to leave an organic phase and heating said organic phase to a temperature not lower than 80° C. to cause rearrangement of the acid azide to thereby obtain an isocyanate solution;
   (d) hydrolyzing said isocyanate solution in sulfuric acid having a concentration of 40–80%, to thereby form a salt of 2,2-bis(4-aminophenyl)hexafluoropropane as an aqueous solution mixed with an organic phase, wherein at least 5 mols of sulfuric acid (as $H_2SO_4$) per mol of 2,2-bis(4-carboxyphenyl)-hexafluoropropane are used; and
   (e) separating the aqueous solution formed at step (d) from the organic phase and neutralizing the separated aqueous solution to thereby precipitate 2,2-bis(4-aminophenyl)hexafluoropropane.

2. A process according to claim 1, wherein said organic liquid at step (a) is selected from the group consisting of toluene, xylene and chlorobenzene.

3. A process according to claim 1, wherein said catalyst at step (a) is selected from the group consisting of dimethylformamide and dimethylacetamide.

4. A process according to claim 1, wherein the mixing at step (b) is performed at temperatures in the range from 0° to 40° C.

5. A process according to claim 4, wherein the mixing at step (b) is performed by adding the 2,2-bis(4-chloroformylphenyl)hexafluoropropane solution to the sodium azide solution.

6. A process according to claim 4, wherein the mixing at step (b) is performed in the presence of a phase-transfer catalyst selected from ammonium salts and phosphonium salts.

7. A process according to claim 1, wherein the hydrolysis at step (d) is carried out at a temperature not lower than 80° C.

* * * * *